US011541061B2

(12) United States Patent
Reidenberg et al.

(10) Patent No.: US 11,541,061 B2
(45) Date of Patent: Jan. 3, 2023

(54) NEUROBLASTOMA TREATMENT WITH TAUROLIDINE HYDROLYSIS PRODUCTS

(71) Applicant: CorMedix Inc., Berkeley Heights, NJ (US)

(72) Inventors: Bruce Reidenberg, Rye, NY (US); Robert DiLuccio, Viera, FL (US)

(73) Assignee: CorMedix Inc., Berkeley Heights, NJ (US)

( * ) Notice: Subject to any disclaimer, the term of this patent is extended or adjusted under 35 U.S.C. 154(b) by 0 days.

(21) Appl. No.: 16/554,186

(22) Filed: Aug. 28, 2019

(65) Prior Publication Data

US 2019/0381059 A1    Dec. 19, 2019

Related U.S. Application Data

(63) Continuation-in-part of application No. 15/403,876, filed on Jan. 11, 2017, now abandoned.

(60) Provisional application No. 62/277,243, filed on Jan. 11, 2016, provisional application No. 62/723,618, filed on Aug. 28, 2018.

(51) Int. Cl.
*A61K 31/549* (2006.01)
*A61K 31/18* (2006.01)
*A61K 31/047* (2006.01)
*A61K 9/00* (2006.01)
*A61K 9/14* (2006.01)
*A61K 47/34* (2017.01)

(52) U.S. Cl.
CPC .......... *A61K 31/549* (2013.01); *A61K 9/0019* (2013.01); *A61K 9/14* (2013.01); *A61K 31/047* (2013.01); *A61K 31/18* (2013.01); *A61K 47/34* (2013.01)

(58) Field of Classification Search
None
See application file for complete search history.

(56) References Cited

U.S. PATENT DOCUMENTS

| 5,593,665 | A | ‡ | 1/1997 | Pfirrmann | A61P 35/00 424/85 |
| 5,602,150 | A | ‡ | 2/1997 | Lidsky | A61K 31/55 514/17 |
| 6,521,616 | B2 | ‡ | 2/2003 | Calabresi | A61K 31/541 514/22 |
| 7,638,511 | B2 | * | 12/2009 | Stendel | A61P 43/00 514/222.5 |
| 8,202,860 | B2 | ‡ | 6/2012 | Stendel | A61P 25/00 514/22 |
| 9,012,444 | B2 | ‡ | 4/2015 | Redmond | A61P 35/00 514/22 |
| 9,844,555 | B2 | ‡ | 12/2017 | Pfirrmann | A61K 31/541 |
| 2002/0049200 | A1 | * | 4/2002 | Calabresi | A61K 31/00 514/222.5 |
| 2002/0091123 | A1 | ‡ | 7/2002 | Redmond | A61K 31/54 514/22 |
| 2002/0111345 | A1 | | 8/2002 | Calabresi et al. | |
| 2003/0044911 | A1 | ‡ | 3/2003 | Lerman | C07K 14/705 435/69 |
| 2003/0078257 | A1 | ‡ | 4/2003 | Calabresi | A61K 31/00 514/22 |
| 2004/0176360 | A1 | | 9/2004 | Calabresi et al. | |
| 2005/0096314 | A1 | | 5/2005 | Pfirrmann | |
| 2005/0119254 | A1 | ‡ | 6/2005 | Pfirrmann | A61K 31/541 514/22 |
| 2008/0171738 | A1 | | 7/2008 | Redmond et al. | |
| 2008/0177217 | A1 | ‡ | 7/2008 | Polaschegg | A61P 13/02 604/6 |
| 2013/0085469 | A1 | ‡ | 4/2013 | Polaschegg | A61L 27/54 604/50 |
| 2013/0089606 | A1 | ‡ | 4/2013 | Pfirrmann | A61K 9/2846 424/463 |
| 2014/0140931 | A1 | ‡ | 5/2014 | Yu | A61K 9/5123 424/9 |
| 2017/0056561 | A1 | ‡ | 3/2017 | DiLuccio | A61L 27/54 |
| 2017/0196875 | A1 | | 7/2017 | DiLuccio | |

(Continued)

FOREIGN PATENT DOCUMENTS

DE   102010010360     9/2011
EP        1066830  ‡  1/2001

(Continued)

OTHER PUBLICATIONS

McCall E.E. et al., Maternal Hair Dye Use and Risk of Neuroblastoma in Offspring, Cancer Causes and Control, 2005, vol. 16., pp. 743-748.‡

Martinotti S. et al., In Vitro Screening of Synergistic Ascorbate-Drug Combinations for the Treatment of Malignant Mesothelioma, Toxicology in Vitro, 2011, vol. 25, pp. 1568-1574.‡

Pearson A. D.J. et al., High-Dose Rapid and Standard Induction Chemotherapy for Patients Aged Over 1 Year with Stage 4 Neuroblastoma: A Randomised Trial, The Lancet Oncology, 2008, vol. 9, pp. 247-256.‡

Braumann C. et al., Local and Systemic Chemotherapy with Taurolidine and Taurolidine/Heparin in Colon Cancer-Bearing Rats Undergoing Laparotomy, Clinical & Experimental Metastasis, 2003, vol. 20, pp. 387-394.‡

(Continued)

*Primary Examiner* — Erin E Hirt
(74) *Attorney, Agent, or Firm* — Pandiscio & Pandiscio

(57) ABSTRACT

Neuroblastoma is a tumor primarily affecting children. The current standard of care is not curative except in the rare case of a surgically-resectable lesion, although very high survival rates have been documented for low-risk neuroblastoma and moderate-risk neuroblastoma. Taurolidine was developed as an anti-infective, but it has been found to have surprising oncolytic activity in cell cultures and now in a rodent cancer model. The efficacy in rodent model is superior to the efficacy in cell culture. This invention relates to the use of taurolidine hydrolysis products (tarultam and/or taurinamide and/or methylene glycol and/or selected combinations thereof) for the treatment of neuroblastoma in juvenile mammals.

3 Claims, 10 Drawing Sheets

(56) References Cited

U.S. PATENT DOCUMENTS

| | | |
|---|---|---|
| 2018/0185378 A1 | 7/2018 | DiLuccio |
| 2019/0381058 A1 | 12/2019 | Reidenberg et al. |
| 2019/0381059 A1 | 12/2019 | Reidenberg et al. |

FOREIGN PATENT DOCUMENTS

| | | | |
|---|---|---|---|
| WO | WO 91/13628 | ‡ | 9/1991 |
| WO | WO 01/39762 | | 6/2001 |
| WO | WO 03/051902 | ‡ | 6/2003 |
| WO | WO 2005/115357 | | 12/2005 |
| WO | WO 2007/020509 | ‡ | 2/2007 |
| WO | WO 2011/053562 | | 5/2011 |
| WO | WO 2011/151722 | | 12/2011 |
| WO | WO 2013/016696 | | 1/2013 |
| WO | WO 2017/123635 | | 7/2017 |

OTHER PUBLICATIONS

Braumann C. et al., Influence of Intraperitoneal and Systemic Application of Taurolidine and Taurolidine/Heparin During Laparoscopy on Intraperitoneal and Subcutaneous Tumor Growth in Rats, Clinical & Experimental Metastasis, 2001, vol. 18, pp. 547-552.‡
Chromik A.M. et al., Synergistic Effects in Apoptosis Induction by Taurolidine and TRAIL in HCT-15 Colon Carcinoma Cells, Journal of Investigative Surgery, 2007, vol. 20, pp. 339-348.‡
Strenger V. et al., Diagnostic and Prognostic Impact of Urinary Catecholamines in Neuroblastoma Patients, Pediatric Blood & Cancer, 2007, vol. 48, pp. 504-509.‡
Calabresi, P. et al., Taurolidine: Cytotoxic and Mechanistic Evaluation of a Novel Antineoplastic Agent, Cancer Research, 2001, vol. 61, pp. 6816-6821.‡
FDA Guidance for Industry, Estimating the Maximum Safe Starting Dose in Initial Clinical Trials for Therapeutics in Adult Healthy Volunteers, 2005.‡
Bagci, 0. et al., Amplification of Cellular Oncogenes in Solid Tumors, N Am J Med Sci., 2015, vol. 7, No. 8, pp. 341-346.‡
CorMedix press release, Cormedix Inc. Announces Agreement With Nanoproteagen for Its Proprietary Nanoparticle Technology, NanoproTM, in Combination With CRMD-005 for Pediatric Neuroblastoma, 2016.‡
Luckert, C. et al., Taurolidine Specifically Inhibits Growth of Neuroblastoma Cell Lines In Vitro, Journal of Pediatric Hematology/Oncology, 2014, vol. 36, No. 4, pp. e219-e223.‡
Patil, Y. et al., Nanoparticle-mediated simultaneous and targeted delivery of paclitaxel and tariquidar overcomes tumor drug resistance, Journal of Controlled Release, 2009, vol. 136, pp. 21-29.‡
Kreissman, S.G. et al., Response and Toxicity to a Dose-Intensive Multi-Agent Chemotherapy Induction Regimen for High Risk Neuroblastoma (HR-NB): A Children's Oncology Group (COG A3973) Study, Abstract, Journal of Clinical Oncology, 2016, vol. 25, No. 18 Supplement.‡
Aceto, N. et al., Taurolidine and oxidative stress: a rationale for local treatment of mesothelioma, European Respiratory Journal, 2009, vol. 34, No. 6, pp. 1399-1407.‡
Baker, D.L. et al., A Phase III Trial of Biologically-Based Therapy Reduction for Intermediate Risk Neuroblastoma, Abstract, Journal of Clinical Oncology, 2016, vol. 25, No. 18 Supplement.‡
Tsuda, H. et al., Retrospective study on amplification of N-myc and c-myc genes in pediatric solid tumors and its association with prognosis and tumor differentiation, Abstract, Lab Invest. 1988, vol. 59, No. 3, pp. 321-327.‡
Wong, H.L. et al., Simultaneous delivery of doxorubicin and GG918 (Elacridar) by new Polymer-Lipid Hybrid Nanoparticles (PLN) for enhanced treatment of multidrug-resistant breast cancer, Journal of Controlled Release, 2006, vol. 116, pp. 275-284.‡
Tansey, W.P., Mammalian MYC Proteins and Cancer, New Journal of Science, 2014.‡
Stendel, R. et al., Enhancement of Fas-Ligand-Mediated Programmed Cell Death by Taurolidine, Abstract, Anticancer Research, 2003, vol. 23.‡
Marley, K. et al., Pharmacokinetic study and evaluation of the safety of taurolidine for dogs with osteosarcoma, Journal of Experimental & Clinical Cancer Research, Oct. 11, 2013, vol. 32, No. 74, pp. 1-24.‡
Reidenberg, B. E. et al., Postmarketing experience with Neutrolin (taurolidine, heparin, calcium citrate) catheter lock solution in hemodialysis patients, European Journal of Clinical Microbiology & Infectious Diseases,Dec. 6, 2017, vol. 37, pp. 661-663.‡
Swift, L. et al., Dual functionality of the antimicrobial agent taurolidine which demonstrates effective anti-tumor properties in pediatric neuroblastoma, Investigational New Drugs, Jul. 2, 2019.‡
Boyer, I. J. et al., Formaldehyde and Methylene Glycol, Oct. 12, 2011, pp. 1-41.‡
Daigeler A. et al., Synergistic Apoptotic Effects of Taurolidine and TRAIL on Squamous Carcinoma Cells of the Esophagus, International Journal of Oncology, 2008, vol. 32, pp. 1205-1220.‡
Clinical trial No. NCT01175356, Induction Therapy Including 131 I-MIBG and Chemotherapy in Treating Patients with Newly Diagnosed High-Risk Neuroblastoma Undergoing Stem Cell Transplant, Radiation Therapy, and Maintenance Therapy with Isotretinoin, https://clinicaltrials.gov/ct2/show/NCT01175356.‡
Brodeur G.M. et al., Amplification of N-myc in Untreated Human Neuroblastomas Correlates with Advanced Disease Stage, SCIENCE, Jun. 8, 1984, vol. 224, pp. 1121-1124.‡
NANT home page, http://www.nant.org.‡
Kushner B.H. et al., Irinotecan Plus Temozolomide for Relapsed or Refractory Neuroblastoma, Journal of Clinical Oncology, Nov. 20, 2006, vol. 24, No. 33, pp. 5271-5276.‡
Ladenstein R. et al., Randomized Trail of Prophylactic Granulocyte Colony-Stimulating Factor During Rapid COJEC Induction in Pediatric Patients with High-Risk Neuroblastoma: The European HR-NBL1/SIOPEN Study, Jul. 20, 2010, vol. 28, No. 21, pp. 3516-3524.‡
Eschenburg G. et al., Taurolidine Cooperates with Antineoplastic Drugs in Neuroblastoma Cells, Genes & Cancer, Oct. 9, 2014, vol. 5, Nos. 11-12, pp. 460-469.‡
Olshan A.F. et al., Hormone and Fertility Drug Use and the Risk of Neuroblastoma: A Report from the Children's Cancer Group and the Pediatric Oncology Group, American Journal of Epidemiology, 1999, vol. 150, No. 9, pp. 930-938.‡
Clinical trial No. NCT00410631, Observation, Combination Chemotherapy, Radiation Therapy, and/or Autologous Stem Cell Transplant in Treating Young Patients with Neuroblastoma, https://clinicaltrials.gov/ct2/show/NCT00410631.‡
Diskin S.J. et al., Copy Number Variation at 1q21.1 Associated with Neuroblastoma, Nature, Jun. 18, 2009, vol. 459, No. 7249, pp. 987-991.‡
Karlisch C. et al., Effects of TRAIL and Taurolidine on Apoptosis and Proliferation in Human Rhabdomyosarcoma, Leiomyosarcoma and Epithelioid Cell Sarcoma, International Journal of Oncology, 2013, vol. 42, pp. 945-956.‡
Harati K. et al., TRAIL and Taurolidine Enhance the Anticancer Activity of Doxorubicin, Trabectedin and Mafosfamide in HT1080 Human Fibrosarcoma Cells, Anticancer Research, 2012, vol. 32, pp. 2967-2984.‡
Menegaux F. et al., Day Care, Childhood Infections, and Risk of Neuroblastoma, American Journal of Epidemiology, 2004, vol. 159, No. 9, pp. 843-851.‡
Berthold F. et al., Myeloablative Megatherapy with Autologous Stem-Cell Rescue Versus Oral Maintenance Chemotherapy as Consolidation Treatment in Patients with High-Risk Neuroblastoma: A Randomised Controlled Trial, The Lancet Oncology, Sep. 2005, vol. 6, pp. 649-668.‡
Matthay K.K. et al., Long-Term Results for Children with High-Risk Neuroblastoma Treated on a Randomized Trial of Myeloablative Therapy Followed by 13-cis-Retinoic Acid: A Children's Oncology Group Study, Journal of Clinical Oncology, Mar. 1, 2009, vol. 27, No. 7, pp. 1007-1013.‡
Baker D.L. et al., Outcome After Reduced Chemotherapy for Intermediate-Risk Neuroblastoma, New England Journal of Medicine, Sep. 30, 2010, vol. 363, No. 14, pp. 1313-1323.‡

(56) References Cited

OTHER PUBLICATIONS

Veronese et al., PEGylation, successful approach to drug delivery, DDT, vol. 10, No. 21, 2005, pp. 1451-1458.‡
Wickstrom et al., Wnt/3-catenin pathway regulates MGMT gene expression in cancer and inhibition of Wnt signaling prevents chemoresistance, Nature Communications, 2015.‡
Wagner et al., Targeting Methylguanine-DNA Methyltransferase in the Treatment of Neuroblastoma, Clinical Cancer Research, vol. 13, No. 18, 2007, pp. 5418-5425.‡
Brodeur, Neuroblastoma: Biological Insights Into a Clinical Enigma, Nature Reviews Cancer, vol. 3, 2003, pp. 203-216.‡
Maris, Recent Advances in Neuroblastoma, New England Journal of Medicine, 2010, pp. 2202-2211. Mayo Clinic, Neuroblastoma, https://www.mayoclinic.org/diseases-conditions/neuroblastoma/symptoms-causes/syc-20351017.‡
American Cancer Society, What is Neuroblastoma?, 2018 https://www.cancer.org/cancer/neuroblastoma/about/what-is-neuroblastoma.html.‡
Arcangeli and Becchetti, "Novel perspectives in cancer therapy: Targeting ion channels" Drug Resistance Updates 21-22: 11-19 (2015) (Year: 2015).‡
Plantone et al., "Neurological disease associated with autoantibodies targeting the voltage-gated potassium channel complex: immunobiology and clinical characteristics", Neuroimmunol Neuroinflammation 3: 69-78 (2016) (Year: 2016).‡
Wohlfart et al., "Efficient Chemotherapy of Rat Glioblastoma using Doxorubicin-loaded PLGA Nanoparticles with Different Stabilizers", PLoS ONE 6: e19121 (2011) (Year: 2011).‡
Neary et al., "The Evolving Role of Taurolidine in Cancer Therapy", Ann Sur Oncol 17: 1135-1143 (2010) (Year: 2010).‡
Harati et al., "TRAIL and Taurolidine Enhance the Anticancer Activity of Doxorubicin, Trabectedin and Mafosfamide in HT1080 Human Fibrosarcoma Cells", Anticancer Res 32: 2967-2984 (2012) (Year: 2012).‡
Eschenburg et al., "Taurolidine cooperates with antineoplastic drugs in neuroblastoma cells", Genes & Cancer 5: 460-469 (2014) (of record) (herein, Eschenburg) (Year: 2014).‡
Gong et al. "The pharmacokinetics of taurolidine metabolites in healthy volunteers", J Clin Pharmacol 47: 697-703 (2007) (Year: 2007).‡
Ma, L.; Kohli, M.; Smith, A. "Nanoparticles for Combination Drug Therapy" ACS Nano, 2013, 7(11), 9518-9525. Accessed via NIH Public access manuscript pagination, 1-8, (Year: 2013).‡
DeCroes, O. G. "Development of poly(lactic acid)-poly(ethylene glycol) nanoparticles for the delivery. . . " Clemson University Press, M.S. Thesis, 2014. (Year: 2014).‡
Eschenburg, G. et al. "Taurolidine cooperates with antineoplastic drugs in neuroblastoma cells" Genes & Cancer, 2014, 5(11-12), 460-469. (Year: 2014).‡
Tivnan et al. (PLoS ONE 2012, 7(5), e38129) (Year: 2012).‡
Mishra et al (J. Ped. Neurosci., 2018, 13(3), 366-370 (Year: 2018).‡
Zhu et al. (Chin. J. Cancer, 2015, 34, 49). (Year: 2015).‡
Matthay, K. K. "Neuroblastoma: biology and therapy" Oncology, 1997, 11(12), 1857-1866 (abstract only). (Year: 1997).‡
Cosmetic Ingredient Review, Formaldehyde and Methylene Glycol, 2011.
George R.E. et al., High-Risk Neuroblastoma Treated with Tandem Autologous Peripheral-Blood Stem Cell-Supported Transplantation: Long-Term Survival Update, Journal of Clinical Oncology, Jun. 20, 2006, vol. 24, No. 18, pp. 2891-2896.
Gisselsson D. et al., Distinct Evolutionary Mechanisms for Genomic Imbalances in High-Risk and Low-Risk Neuroblastomas, Journal of Carcinogenesis, Sep. 26, 2007, vol. 6, No. 15, pp. 1-8.

Maris, Recent Advances in Neuroblastoma, New England Journal of Medicine, 2010, pp. 2202-2211.
Mayo Clinic, Neuroblastoma, 2020, https://www.mayoclinic.org/diseases-conditions/neuroblastoma/symptoms-causes/syc-20351017.
Mishra et al. Primary Pediatric Intracranial Neuroblastoma: A Report of Two Cases, Jounral of Pediatric Neurosciences, vol. 13, No. 3, 2018, pp. 366-370.
Pritchard J. et al., High Dose Melphalan in the Treatment of Advanced Neuroblastoma: Results of a Randomised Trial (ENSG-1) by the European Neuroblastoma Study Group, Pediatric Blood & Cancer, 2005, vol. 44, pp. 348-357.
Tivnan et al., Inhibition of Neuroblastoma Tumor Growth by Targeted Delivery of MicroRNA-34a Using Anti-Disialoganglioside GD2 Coated Nanoparticles, PLoS ONE, vol. 7, No. 5, 2012.
Wang K. et al., Integrative Genomics Identifies LMO1 as a Neuroblastoma Oncogene, Nature, Jan. 13, 2011, vol. 469, No. 7329, pp. 216-220.
Wickstrom et al., Wnt/β-catenin pathway regulates MGMT gene expression in cancer and inhibition of Wnt signaling prevents chemoresistance, Nature Communications, 2015.
Zhu et al., Brain metastasis in children with stage 4 neuroblastoma after multidisciplinary treatment, Chinese Journal of Cancer, vol. 34, No. 49, 2015.
Braumann C. et al., Taurolidine reduces the tumor stimulating cytokine interleukin-1beta in patients with resectable gastrointestinal cancer: a multicentre prosepective randomized trial, World Journal of Surgical Oncology, 2009, vol. 7, p. 30.
Fangyuan et al. "Progress in the study of poly (lactide-co-glycolide) nanoparticles for anticancer agents delivery", Northwest Pharmaceutical Journal, 2013, vol. 28, No. 6, pp. 656-660.
Farrington, M., Chemotherapy of Infections, Clinical Pharmacology, 2012.
Hato et al. (Clin. Cancer Res., 2014, 20, 2831-2837). (Year: 2014).
Kohane, D.S. et al., Microparticles and Nanoparticles for Drug Delivery, Biotechnology and Bioengineering, Dec. 28, 2006, vol. 96, No. 2, pp. 203-209.
Monson et al. "Taurolidine inhibits tumor necrosis factor (TNF) toxicity-new evidence of TNF and endotoxin synergy", Eur J Surg Oncol, Jun. 1993, vol. 19, No. 3, pp. 226-231.
Mudshinge, S. R. et al. "Nanoparticles: emerging carriers for drug delivery" Saudi Pharmaceutical Journal, 2011, 19, 129-141.
Principles of Manual Medicine (Feb. 19, 2015, hllp://web.archive.org/web/20150219091248/hllp://hal.bim.msu.edu:80/cmeonline/Autonomic/start.html) (Year: 2015).
Rasenack et al., Micron-size drug particles: common and novel micronization techniques, 2004, vol. 9, No. 1.
Reidenberg B. et al., Multi-Resistant Candida auris is Susceptible To Taurlidine, Aspergillus & Aspergillosis, 2017.
Simon et al., J. Cancer Res. Clin. Oneal., 2007, 133, 653-661.
Wong et al., "The cytotoxic effects of lipidic formulated gold porphyrin nanoparticles for the treatment of neuroblastoma", Nanotechnology, Science and Applications, Jun. 17, 2010, pp. 23-28.
Buchholz et al., Effectivity and Toxicity of Taurultam (TRLT) as Anti-Neoplasticagent in Malignant Tumor Cells—In Vitro Study of Pancreatic and Colon Cancer Cell Lines, German Medical Science GMS Publishing House, Apr. 2013.
Mohler et al., Redox-directed cancer therapeutics: Taurolidine and Piperlongumine as broadly effective antineoplastic agents, International Journal of Oncology, vol. 45, 2014, pp. 1329-1336.
Stendel et al., Pharmacokinetics of Taurolidine following Repeated Intravenous Infusions Measured by HPLC-ESI-MS/MS of the Derivates Taurultame and Taurinamide in Glioblastoma Patients, Clinical Pharmacokinetics, vol. 46, No. 6, 2007, pp. 513-524.

\* cited by examiner
‡ imported from a related application

Note: percent survival is percent survival of the animal (not the tumor).

Mean Pharmacokinetic Parameters of Taurinamide

| Duration of infusion hr | n | AUC$_{(0-24)}$ hr*µg/mL | AUC$_{(0-\infty)}$ hr*µg/mL | C$_{max}$ µg/mL | half life hr | T$_{max}$ hr |
|---|---|---|---|---|---|---|
| 2 | 6 | 315.4 ± 46.5 | 356.5 ± 61.1 | 53.9 ± 10.8 | 6.9 ± 1.5 | 2.00 |
| 1 | 5 | 233.9 ± 29.4 | 269.0 ± 35.3 | 59.4 ± 19.4 | 6.5 ± 1.4 | 1.00 |
| 0.5 | 6 | 271.7 ± 61.4 | 310.3 ± 67.2 | 62.6 ± 16.8 | 6.7 ± 1.2 | 0.63 |
| All Groups | | 273.4 ± 55.8 | 312.7 ± 63.2 | 57.3 ± 15.3 | 6.7 ± 1.3 | 1.00* |

All data are presented as mean ± S.D.
\* = median

FIG. 10

Mean Pharmacokinetic Parameters of Taurolism

| Duration of infusion hr | n | AUC$_{(0-24)}$ hr*µg/mL | AUC$_{(0-\infty)}$ hr*µg/mL | C$_{max}$ µg/mL | half life hr | T$_{max}$ hr |
|---|---|---|---|---|---|---|
| 2 | 6 | 34.9 ± 9.6 | 35.7 ± 9.0 | 16.0 ± 4.5 | 1.1 ± 0.3 | 1.50 |
| 1 | 5 | 37.3 ± 10.1 | 40.7 ± 11.2 | 32.0 ± 16.1 | 1.2 ± 0.7 | 0.75 |
| 0.5 | 6 | 44.8 ± 9.8 | 51.8 ± 10.6 | 51.4 ± 12.2 | 2.1 ± 1.1 | 0.50 |
| All Groups | | 38.8 ± 9.8 | 42.9 ± 11.4 | 32.0 ± 17.9 | 1.5 ± 0.9 | 0.50* |

All data are presented as mean ± S.D.
\* = median

FIG. 11

NEUROBLASTOMA TREATMENT WITH TAUROLIDINE HYDROLYSIS PRODUCTS

REFERENCE TO PENDING PRIOR PATENT APPLICATIONS

This patent application:

(i) is a continuation-in-part of prior U.S. patent application Ser. No. 15/403,876, filed Jan. 11, 2017 by CorMedix Inc. and Robert DiLuccio for THERAPEUTIC NANOPARTICLES FOR THE TREATMENT OF NEUROBLASTOMA AND OTHER CANCERS, which patent application claims benefit of prior U.S. Provisional Patent Application Ser. No. 62/277,243, filed Jan. 11, 2016 by CorMedix Inc. and Robert DiLuccio for NANOPARTICLE SYSTEM FOR THE TREATMENT OF NEUROBLASTOMA; and (ii) claims benefit of prior U.S. Provisional Patent Application Ser. No. 62/723,618, filed Aug. 28, 2018 by Cormedix Inc. and Bruce Reidenberg et al. for NEUROBLASTOMA TREATMENT WITH TAUROLIDINE HYDROLYSIS PRODUCTS.

The three (3) above-identified patent applications are hereby incorporated herein by reference.

FIELD OF THE INVENTION

This invention relates to therapeutic methods and compositions in general, and more particularly to therapeutic methods and compositions for the treatment of neuroblastoma in a juvenile mammalian body.

BACKGROUND OF THE INVENTION

Neuroblastoma (NB) is the most common extracranial solid cancer in childhood and the most common cancer in infancy, with an incidence of about six hundred fifty cases per year in the U.S., and a hundred cases per year in the UK. Nearly half of neuroblastoma cases occur in children younger than two years. It is a neuroendocrine tumor, arising from any neural crest element of the sympathetic nervous system (SNS). Neuroblastoma most frequently originates in one of the adrenal glands, but can also develop in nerve tissues in the neck, chest, abdomen, or pelvis. Note that while neuroblastoma arises from nerve tissues, it is not a tumor of the central nervous system (CNS).

Neuroblastoma is one of the few human malignancies known to demonstrate spontaneous regression from an undifferentiated state to a completely benign cellular appearance.

Neuroblastoma is a disease exhibiting extreme heterogeneity, and is stratified into three risk categories: low-risk, intermediate-risk, and high-risk. Low-risk neuroblastoma is most common in infants and good outcomes are common with observation only or surgery, whereas high-risk neuroblastoma is difficult to treat successfully even with the most intensive multi-modal therapies available.

When the neuroblastoma lesion is localized, it is generally curable. However, long-term survival for children older than 18 months of age with advanced disease of age is poor, despite aggressive multimodal therapy, e.g., intensive chemotherapy, surgery, radiation therapy, stem cell transplant, differentiation agent isotrentinoin (also called 13-cis-retinoic acid), and frequently immunotherapy with anti-GD2 immunotherapy with anti-GD2 monoclonal antibody therapy.

Biologic and genetic characteristics have been identified which, when added to classic clinical staging, has allowed patient assignment to risk groups for planning treatment intensity. These criteria include age of the patient, extent of disease spread, microscopic appearance, and genetic features including DNA ploidy and N-myc oncogene amplification (N-myc regulate micro RNAs). These criteria are used to classify the neuroblastoma into low-risk, intermediate-risk, and high-risk disease. A recent biology study (COG ANBL00B1) analyzed 2,687 neuroblastoma patients and the spectrum of risk assignment was determined: 37% of neuroblastoma cases are low-risk, 18% of neuroblastoma cases are intermediate-risk, and 45% of neuroblastoma cases are high-risk. Note that there is some evidence that the high- and low-risk types of neuroblastoma are caused by different mechanisms, and are not merely two different degrees of expression of the same mechanism.

The therapies for these different risk categories are very different.

Low-risk neuroblastoma can frequently be observed without any treatments at all or cured with surgery alone.

Intermediate-risk neuroblastoma is generally treated with surgery and chemotherapy.

High-risk neuroblastoma is generally treated with intensive chemotherapy, surgery, radiation therapy, bone marrow/hematopoietic stem cell transplantation, biological-based therapy with 13-cis-retinoic acid (isotretinoin or Accutane) and antibody therapy (usually administered with the cytokines GM-CSF and IL-2. cytokines).

With current treatments, patients with low-risk neuroblastoma and intermediate-risk neuroblastoma have an excellent prognosis, with cure rates above 90% for low-risk neuroblastoma and 70-90% cure rates for intermediate-risk neuroblastoma. In contrast, therapy for high-risk neuroblastoma over the past two decades has resulted in cures only about 30% of the time. The addition of antibody therapy has raised survival rates for high-risk neuroblastoma significantly. In March 2009, an early analysis of a Children's Oncology Group (COG) study with 226 high-risk neuroblastoma patients showed that two years after stem cell transplant 66% of the group randomized to receive ch14.18 antibody with GM-CSF and IL-2 were alive and disease-free compared to only 46% in the group that did not receive the antibody. The randomization was stopped so all patients enrolling in the trial could receive the antibody therapy.

Chemotherapy agents used in combination have been found to be effective against neuroblastoma. Agents commonly used in induction and for stem cell transplant conditioning are platinum compounds (cisplatin, carboplatin), alkylating agents (cyclophosphamide, ifosfamide, melphalan, topoisomerase II inhibitor) and vinca alkaloids (vincristine). Some newer regimens include topoisomerase I inhibitors (topotecan and irinotecan) in induction which have been found to be effective against recurrent disease.

However, a need exists for a new method and composition which are effective against neuroblastoma.

SUMMARY OF THE INVENTION

In accordance with the present invention, selected hydrolysis products of taurolidine are used to treat neuroblastoma. The selected hydrolysis products of taurolidine may comprise at least one from the group consisting of:
taurinamide;
taurultam;
methylene glycol;
taurultam and taurinamide in a ratio of 1 taurultam:7 taurinamide; and taurultam, taurinamide and methylene glycol in a ratio of 1 taurultam:7 taurinamide:1 methylene glycol.

The taurinamide is given with a dosage range of from 5 mg/kg to 280 mg/kg, with optimal range between 5 mg/kg and 60 mg/kg, from once daily through weekly, for an effective period of time based on individual patient response.

The taurultam is given with a dosage range of from 5 mg/kg to 280 mg/kg, with optimal range between 5 mg/kg and 60 mg/kg, from once daily through weekly, for an effective period of time based on individual patient response.

The methylene glycol is given with a dosage range of from 2.5 mg/kg to 160 mg/kg, with optimal range between 2.5 mg/kg and 30 mg/kg, from once daily through weekly, for an effective period of time based on individual patient response.

The taurultam and taurinamide (in a ratio of 1 taurultam:7 taurinamide) is given with a dosage range of Taurultam from 5 mg/kg to 280 mg/kg, with optimal range between 5 mg/kg and 40 mg/kg, combined with Taurinamide from 5 mg/kg to 280 mg/kg, with optimal range from 35 mg/kg to 40 mg/kg, from once daily through weekly, for an effective period of time based on individual patient response.

The taurultam, taurinamide and methylene glycol (in a ratio of 1 taurultam:7 taurinamide:1 methylene glycol) is given with a dosage range of Taurultam from 5 mg/kg to 280 mg/kg, with optimal range between 5 mg/kg and 40 mg/kg, combined with Taurinamide with a dosage range of from 5 mg/kg to 280 mg/kg, with optimal range from 35 mg/kg to 40 mg/kg, further combined with methylene glycol with a dosage range of from 2.5 mg/kg to 160 mg/kg, with optimal range from 5 mg/kg to 40 mg/kg, from once daily through weekly, for an effective period of time based on individual patient response.

In one preferred form of the invention, the selected hydrolysis products (i.e., the active ingredients) can be delivered systemically in a "shielded form" so that they can reach the site of the neuroblastoma without premature degradation.

More particularly, in one preferred form of the invention, the hydrolysis products can be delivered in the form of a nanoparticle, where the nanoparticle comprises a core of the hydrolysis product and an exterior coating which is configured to prevent premature exposure of the hydrolysis product prior to the arrival of the nanoparticle to the tumor site. The exterior coating breaks down as the nanoparticle travels from the site of the insertion to the site of the tumor so as to release the hydrolysis product intact at the site of the tumor. In one preferred form of the invention, the coating comprises an absorbable polymer or lipid which breaks down as the nanoparticle travels from the site of insertion to the site of the tumor.

In another form of the invention, the hydrolysis products may be delivered using a polymer system which is configured to delay degradation of the active ingredient. By way of example but not limitation, the hydrolysis products may be "pegylated" using polyethylene glycols (PEGs) to delay premature of degradation of the active ingredient.

The selected hydrolysis products of taurolidine can be given systemically, as either a single agent or in combination with other oncolytic agents and/or radiotherapy.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 10 is a chart showing the mean pharmacokinetic parameters of taurinamide; and FIG. 11 is a chart showing the mean pharmacokinetic parameters of taurultam.

DETAILED DESCRIPTION OF THE INVENTION

Taurolidine is a well known antimicrobial with a published mechanism of action and antimicrobial spectrum. Taurolidine is unstable in circulation and therefore has not been successfully developed for systemic infections. Taurolidine has demonstrated efficacy in local application for peritonitis and for prevention of infection when infused as a catheter-lock solution.

Taurolidine has recently been investigated for oncolytic activity and found to have inhibitory effect on cell lines in culture, in combination with standard chemotherapy or alone. Despite claims that in vitro inhibitory concentrations are clinically achievable, the only published human pharmacokinetic study showed NO measurable concentration of taurolidine in healthy volunteers when 5 grams of taurolidine were given intravenously by 20 minute infusion. This is believed to be due to the rapid hydrolysis of taurolidine when administered systemically in a mammalian body.

Figure 1:
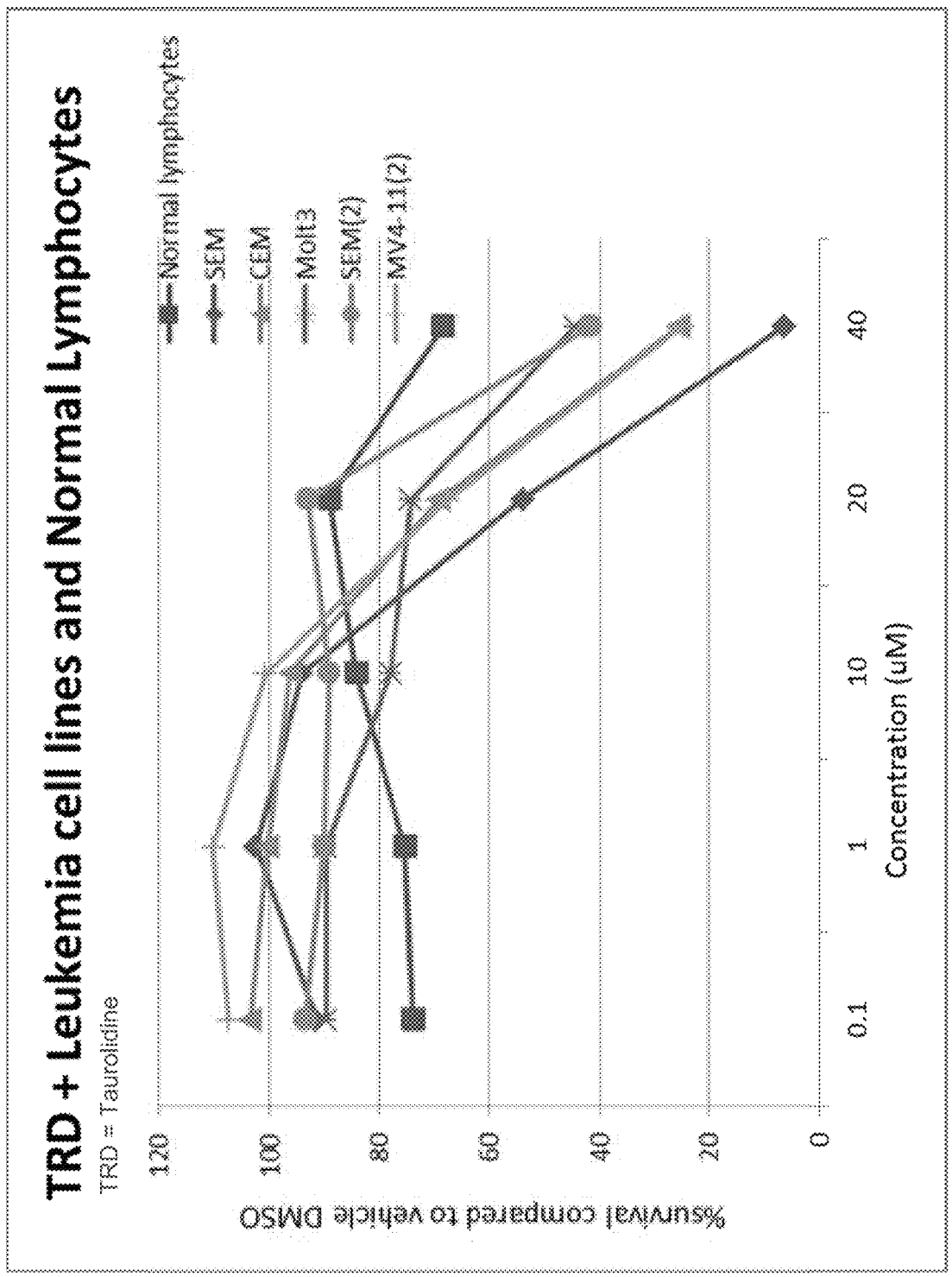
FIG. 1 is a graph showing that leukemia cell lines appear more sensitive to the effects of taurolidine compared to healthy lymphocytes in vitro (not in vivo)

It has been found that leukemia cell lines appear more sensitive to the effects of taurolidine compared to healthy lymphocytes in vitro (not in vivo). See FIG. 1.

It has also been found that neuroblastoma cell lines are more sensitive to a decrease in viability due to taurolidine when compared to healthy fibroblasts in vitro (not in vivo). See FIG. 2.

Furthermore, taurolidine given to CB57 SCID mice with measurable tumors from a neuroblastoma cell line implanted subcutaneously in the CB57 SCID mice showed efficacy in IMR5 tumors and measurable efficacy in SK-N-AS tumors in vivo (not in vitro). See FIGS. 3-6.

Figure 2:
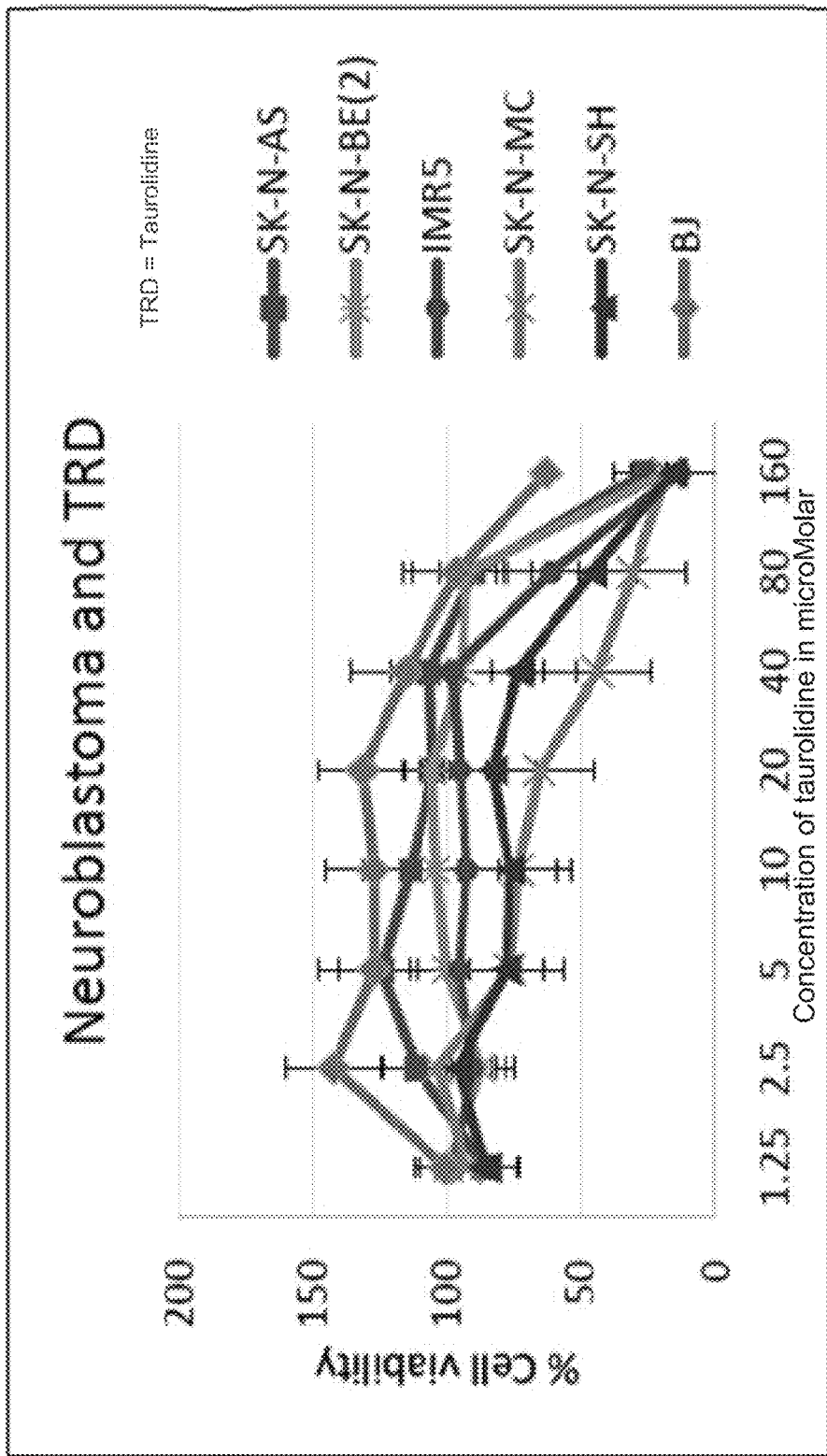
FIG. 2 is a graph showing that neuroblastoma cell lines are more sensitive to a decrease in viability due to taurolidine when compared to healthy fibroblasts (BJ on graph) in vitro (not in vivo)
Figure 3:
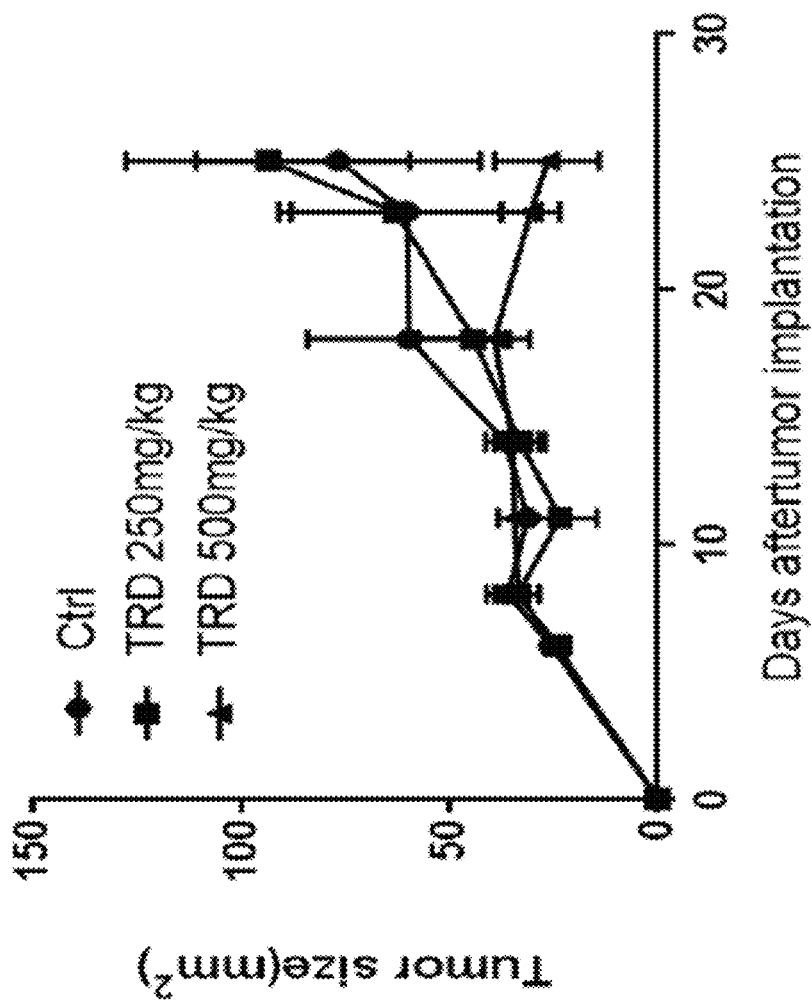
FIGS. 3-6 are graphs or photographs showing that taurolidine given to CB57 SCID mice with measurable tumors from a neuroblastoma cell line implanted subcutaneously in the CB57 SCID mice has efficacy in IMR5 tumors and measurable efficacy in SK-N-AS tumors in vivo (not in vitro)
Figure 4:
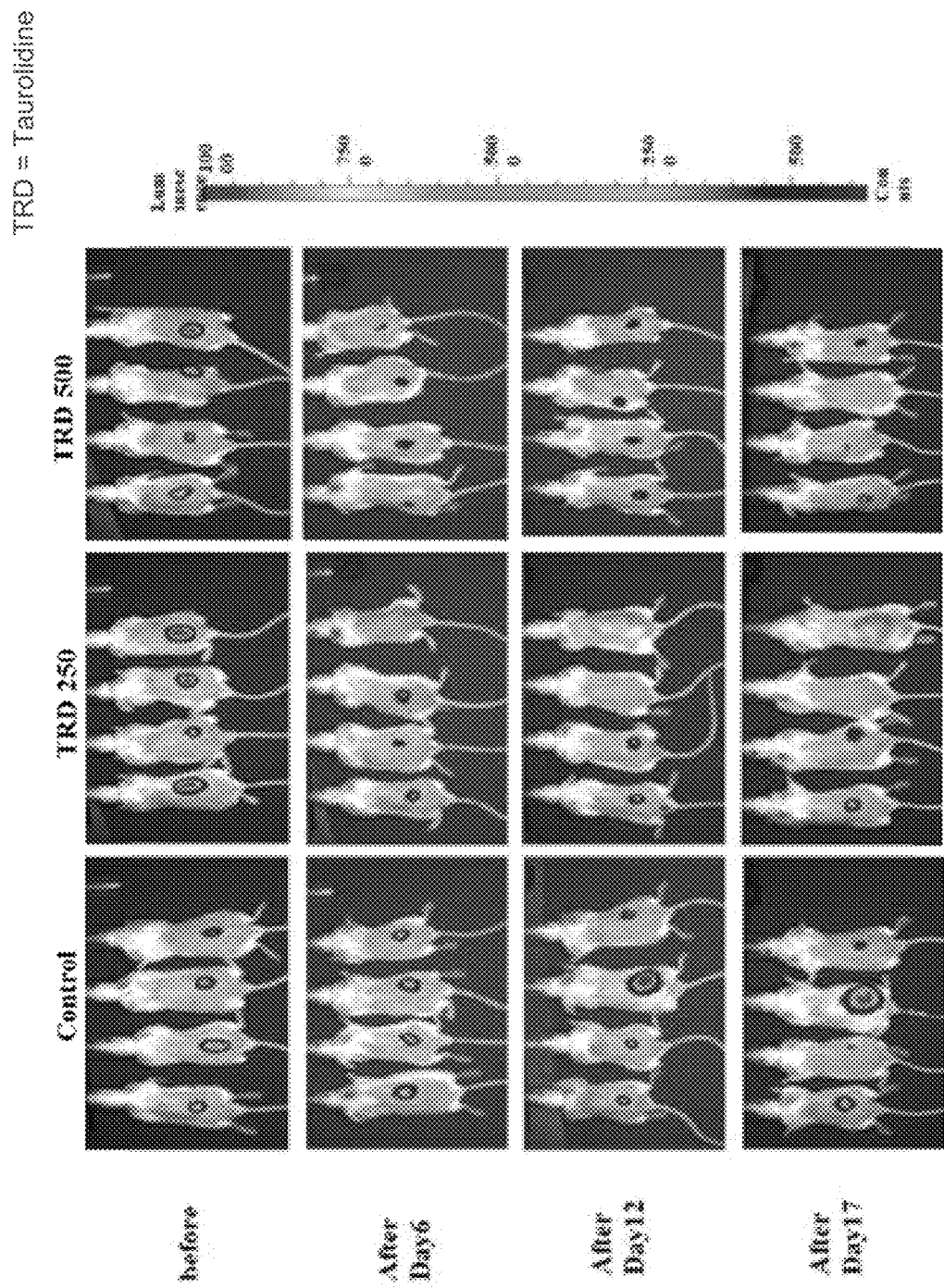
Figure 5:
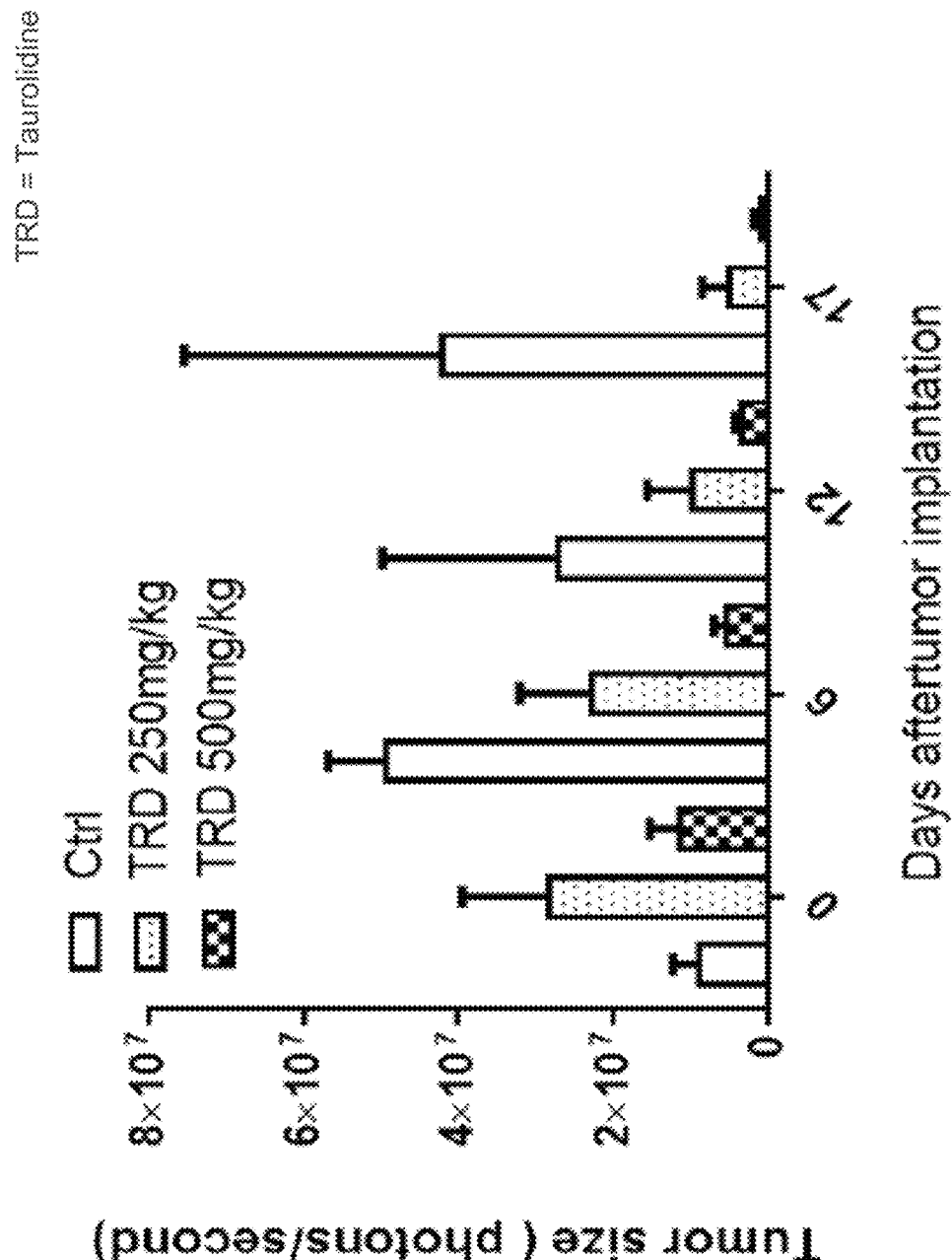
Figure 6:
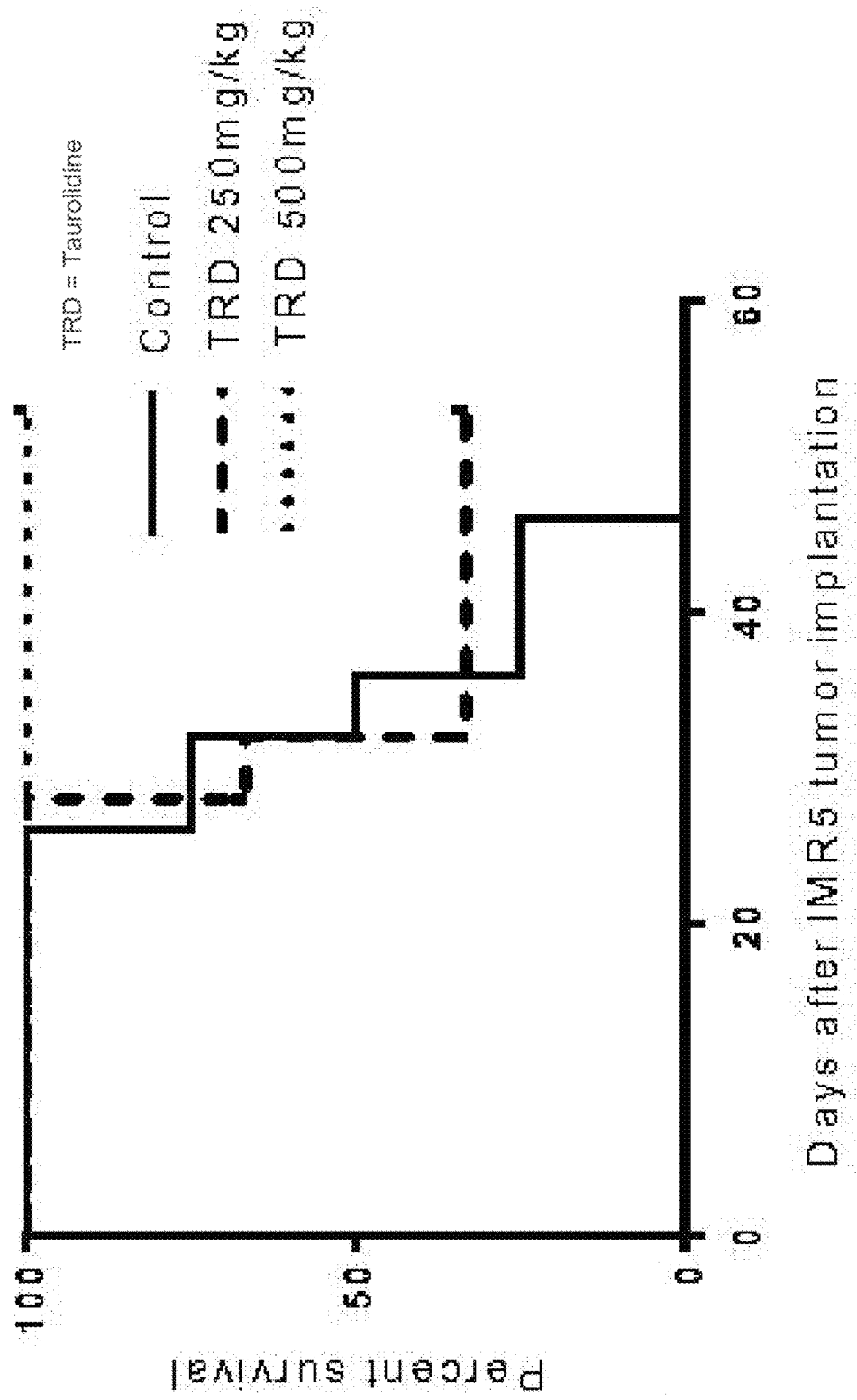

Note that the in vitro efficacy for neuroblastoma cell lines is seen at the highest two concentrations tested, i.e., above 40 microMolar [1 Mole/Liter×284 gm/Mole×1 Mole/1,000,000 microMoles×40 microMolar×1000 mg/gram=11 mg/liter=11 mcg/mL], as seen in FIG. 2 (where only the SK-N-MC cell line, a neuroepithelioma cell line, is below 50% cell viability). The IC50 values are between 80-140 microMolar for neuroblastoma cell lines, and 200 microMolar for normal fibroblasts (see FIG. 2).

The efficacy observed with taurolidine treatment of IMR5 cell implants in vivo (FIGS. 3-6), despite IRM5's relatively high IC50 in vitro (FIG. 2), supports the conclusion that the hydrolysis products of taurolidine may have independent anti-neoplastic activity. In other words, taurolidine treatment of neuroblastoma cells in vivo appears to be significantly more effective than taurolidine treatment of neuroblastoma cells in vitro. Since it is known that taurolidine metabolizes to taurolidine hydrolysis products in vivo, this would support the conclusion that the hydrolysis products of taurolidine may have significant anti-neoplastic activity against neuroblastoma cells. In fact, it may be that the hydrolysis products of taurolidine have higher efficacy against neuroblastoma cells than taurolidine which has not been hydrolyzed.

Figure 7:
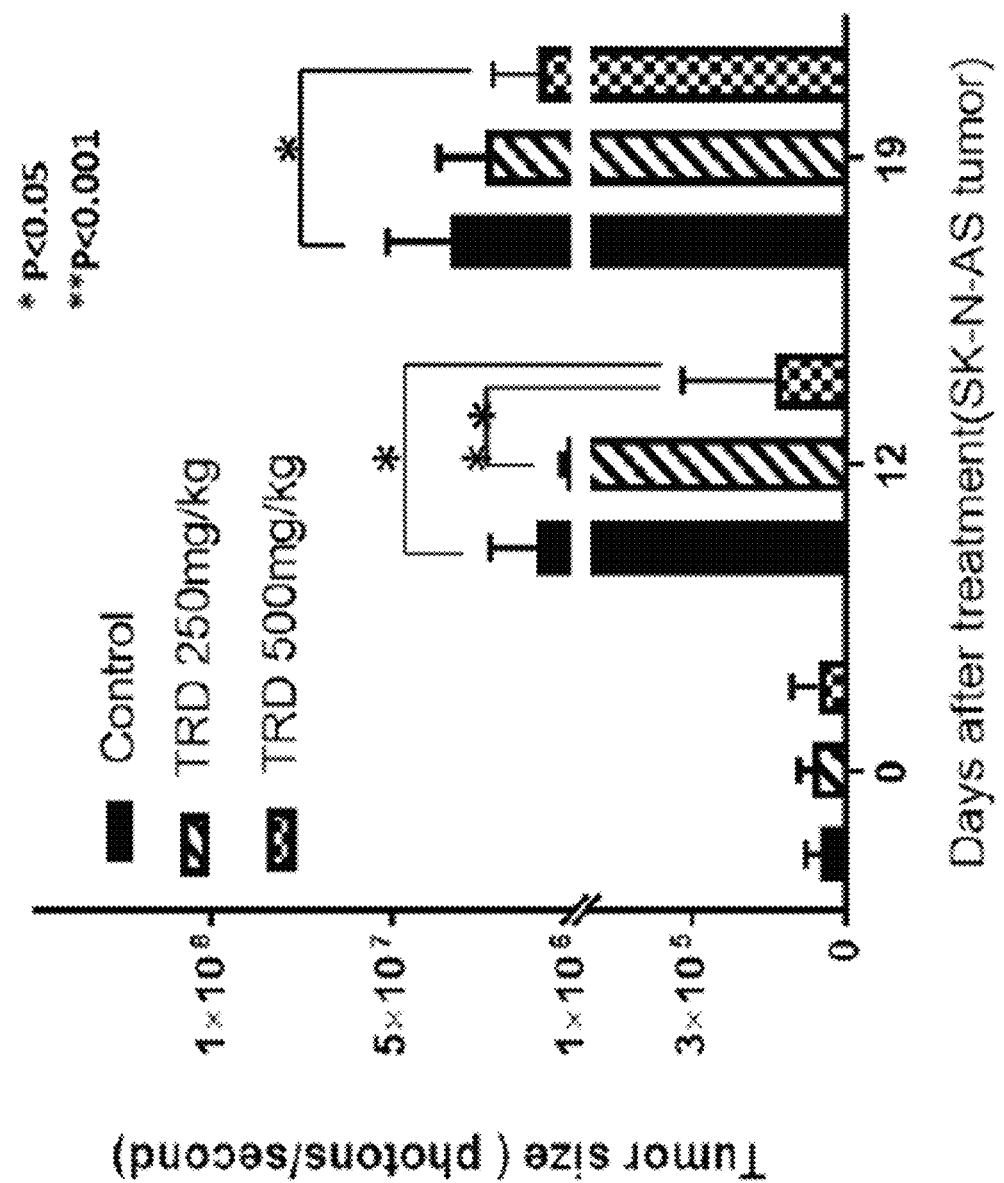
FIGS. 7 and 8 are graphs showing that statistically significant decreases in tumor size were achieved when taurolidine was administered to treat mice with a different cell line (SK-N-AS) also derived from neuroblastoma but overall survival was not significantly different from control.
Figure 8:
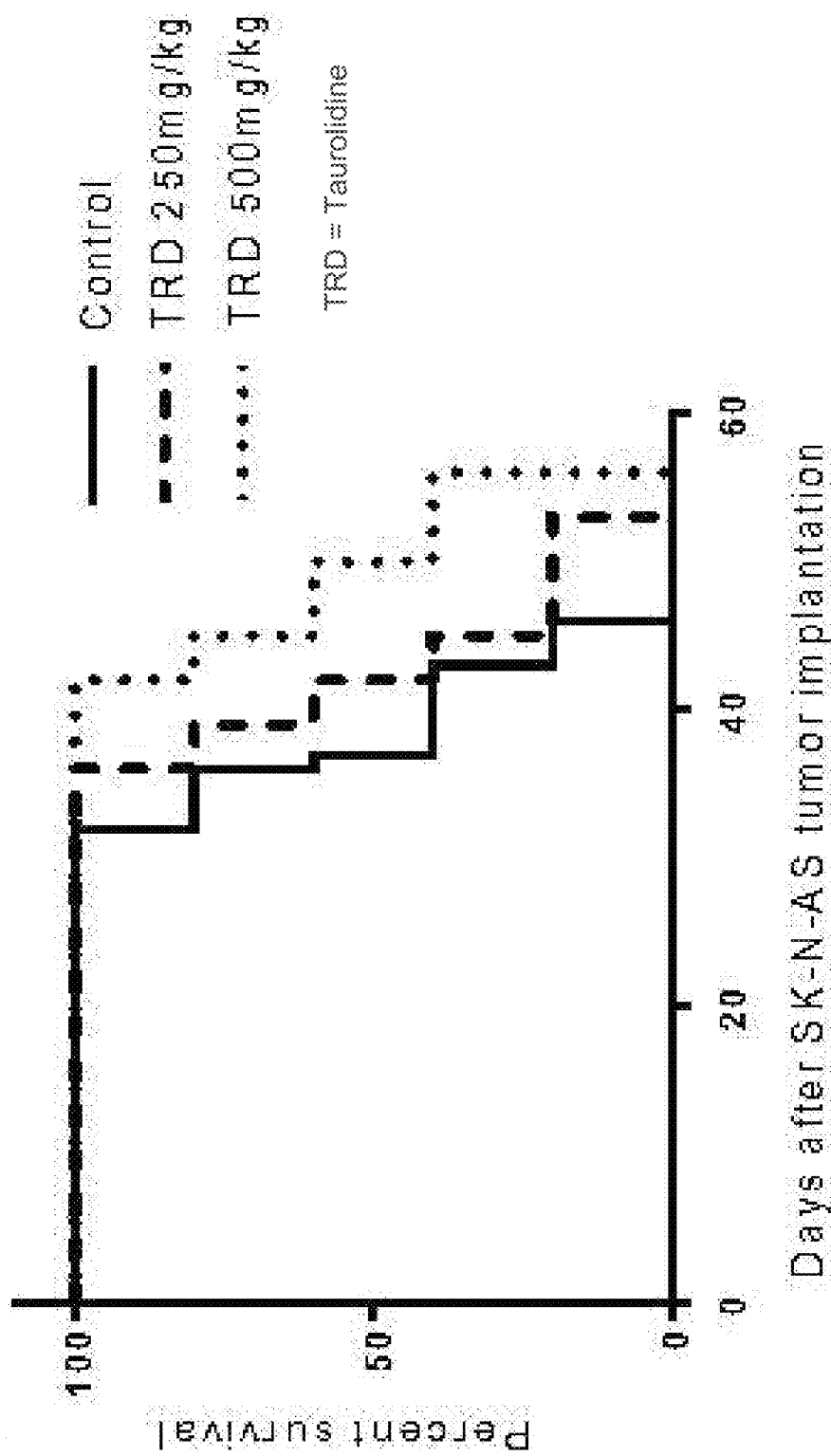

Statistically significant decreases in tumor size were achieved when taurolidine was administered to treat mice with a different cell line (SK-N-AS) also derived from neuroblastoma, though overall survival of the mice implanted with the tumor was not statistically different from the control. See FIGS. 7 and 8.

Figure 9:
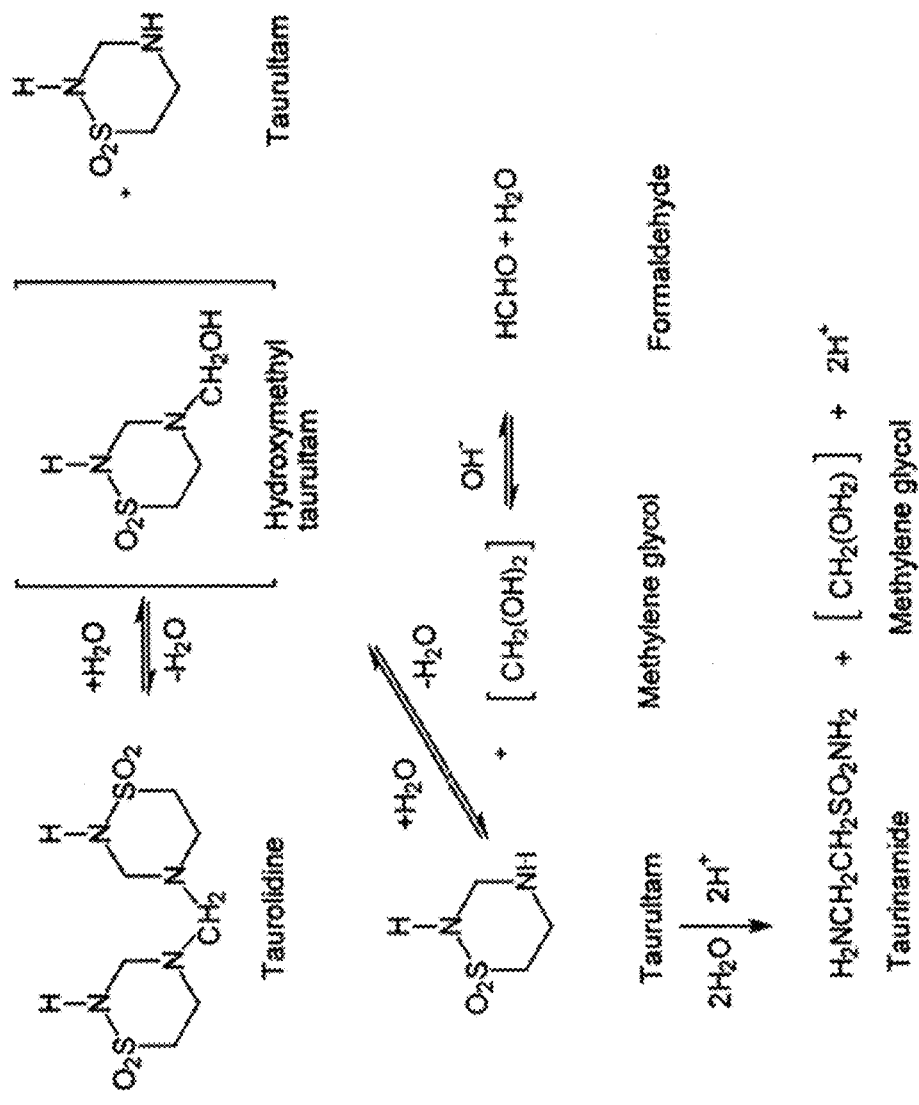
FIG. 9 illustrates the mechanism for the hydrolysis of taurolidine.

It has now been discovered that selected hydrolysis products of taurolidine may be used to treat neuroblastoma. The mechanism for the hydrolysis of taurolidine is shown in FIG. 9. The selected hydrolysis products of taurolidine that may be used to treat neuroblastoma may comprise at least one from the group consisting of:

taurinamide;
taurultum;
methylene glycol;
taurultam and taurinamide in a ratio of 1 taurultam:7 taurinamide; and
taurultam, taurinamide and methylene glycol in a ratio of 1 taurultam:7 taurinamide:1 methylene glycol.

The taurinamide is given with a dosage range of from 5 mg/kg to 280 mg/kg, with optimal range between 5 mg/kg and 60 mg/kg, from once daily through weekly, for an effective period of time based on individual patient response. The mean pharmacokinetic parameters of taurinamide are shown in FIG. 10.

The taurultam is given with a dosage range of from 5 mg/kg to 280 mg/kg, with optimal range between 5 mg/kg and 60 mg/kg, from once daily through weekly, for an effective period of time based on individual patient response. The mean pharmacokinetic parameters of taurultam are shown in FIG. 11.

The methylene glycol is given with a dosage range of from 2.5 mg/kg to 160 mg/kg, with optimal range between 2.5 mg/kg and 30 mg/kg, from once daily through weekly, for an effective period of time based on individual patient response.

The taurultam and taurinamide (in a ratio of 1 taurultam:7 taurinamide) is given with a dosage range of Taurultam from 5 mg/kg to 280 mg/kg, with optimal range between 5 mg/kg and 40 mg/kg, combined with Taurinamide from 5 mg/kg to 280 mg/kg, with optimal range from 35 mg/kg to 40 mg/kg, from once daily through weekly, for an effective period of time based on individual patient response.

The taurultam, taurinamide and methylene glycol (in a ratio of 1 taurultam:7 taurinamide:1 methylene glycol) is given with a dosage range of Taurultam from 5 mg/kg to 280 mg/kg, with optimal range between 5 mg/kg and 40 mg/kg, combined with Taurinamide with a dosage range of from 5 mg/kg to 280 mg/kg, with optimal range from 35 mg/kg to 40 mg/kg, further combined with methylene glycol with a dosage range from 2.5 mg/kg to 160 mg/kg, with optimal range from 5 mg/kg to 40 mg/kg, from once daily through weekly, for an effective period of time based on individual patient response.

Dose selection for the hydrolysis products were calculated as follows:

AUC 0-inf Taurultam/AUC 0-inf Taurinamide=42.9/312.7=0.14

Since the molecular weight difference is only a single methyl group, the use of weight-based AUC does not need to be corrected. Therefore, the target ratio when giving Taurultam and Taurinamide in combination is 0.14 or 1:7. And the target ratio when giving taurultam and taurinamide and methylene glycol in combination is 1:7:1.

Effective dosage was computed by computing the human equivalent dosage from the effective mouse dose using the formula:

[Human equivalent dose=mouse mg/kg dose×1 adult human/12 mice×25 child BSA ratio/37 adult BSA ratio=child dose in mg/kg (https://www.fda.gov/downloads/drugs/guidances/ucm078932.pdf).

In one preferred form of the invention, the selected hydrolysis products (active ingredient) can be delivered systemically in a "shielded form" so that they can reach the site of the neuroblastoma to avoid premature degradation.

More particularly, in one preferred form of the invention, the hydrolysis products can be delivered in the form of a nanoparticle, where the nanoparticle comprises a core of the hydrolysis product and an exterior coating which is configured to prevent premature exposure of the hydrolysis product prior to the arrival of the nanoparticle to the tumor site. The exterior coating breaks down as the nanoparticle travels from the site of insertion to the site of the tumor so as to release the hydrolysis product intact at the site of the tumor. In one preferred form of the invention, the coating comprises an absorbable polymer or lipid which breaks down as the nanoparticle travels from the site of insertion to the site of the tumor. By way of example but not limitation, the coating can be created from combinations of copolymers and multimers derived from polymers structured from 1-lactide, glycolide, e-caprolactone, p-dioxanone, and trimethylene carbonate. The coating may also be associated with glycols such as polyethylene glycols (PEGs), which can either be linear or multi-arm structures.

If desired, the nanoparticle may comprise an excipient (e.g., a buffer for providing enhanced hydrolytic stability of the hydrolysis product within the nanoparticle).

Additionally, if desired, the nanoparticle can further comprise a coating, wherein the coating is configured to target the nanoparticle to the site of a neuroblastoma so as to improve the efficacy of the hydrolysis product for treatment of the neuroblastoma. In one preferred form of the invention, the coating comprises binding molecules which are configured to target delivery of the nanoparticle to specific tissue. By way of example but not limitation, the coating for the nanoparticle comprises a monoclonal antibody against N-type calcium channels (e.g., an anti-N-type calcium channel exofacial Fab fragment) for causing the nanoparticle to bind to neural tissue (e.g., to a neuroblastoma tumor).

In another form of the invention, the hydrolysis products may be delivered using a polymer system which is configured to delay degradation of the active ingredient and/or optimize the release properties of the active ingredient. By way of example but not limitation, the hydrolysis products may be "pegylated" using polyethylene glycols (PEGs) to delay premature of degradation of the active ingredient and/or optimize the release properties of the active ingredient.

The selected hydrolysis products of taurolidine can be given systemically, as either a single agent or in combination with other oncolytic agents and/or radiotherapy. Examples of oncolytic agents that can be combined with the hydrolysis products of taurolidine for systemic delivery are platinum compounds (cisplatin, carboplatin), alkylating agents (cyclophosphamide, ifosfamide, melphalan, topoisomerase II inhibitor), vinca alkaloids (vincristine), and topoisomerase I inhibitors (topotecan and irinotecan).

MODIFICATIONS

While the present invention has been described in terms of certain exemplary preferred embodiments, it will be readily understood and appreciated by those skilled in the art that it is not so limited, and that many additions, deletions and modifications may be made to the preferred embodiments discussed above while remaining within the scope of the present invention.

What is claimed is:

1. A method for treating neuroblastoma, the method comprising:
    administering a composition to a patient, wherein the composition comprises:
        taurultam and taurinamide in a weight ratio of 1 taurultam:7 taurinamide, with a dosage range of taurultam between 5 mg/kg and 40 mg/kg and a dosage range of taurinamide from 35 mg/kg to 280 mg/kg;
        wherein the composition is pegylated using polyethylene glycols (PEGs) to delay premature hydrolysis of the composition; and
        wherein the composition is administered from once daily through weekly, for an effective period of time based on the patient's response.

2. The method according to claim 1 wherein the composition is administered in conjunction with an oncolytic agent and/or radiotherapy.

3. The method according to claim 1 wherein the composition is delivered to the patient using one from the group consisting of parenteral delivery, intramuscular delivery and intravenous delivery.

* * * * *